US009777316B2

(12) United States Patent
Korfhage et al.

(10) Patent No.: US 9,777,316 B2
(45) Date of Patent: Oct. 3, 2017

(54) AMPLIFICATION OF COMPLEX NUCLEIC ACIDS

(75) Inventors: Christian Korfhage, Langenfeld (DE); Evelyn Fisch, Hilden (DE)

(73) Assignee: QIAGEN STRASSE 1, Hilden (DE)

( * ) Notice: Subject to any disclaimer, the term of this patent is extended or adjusted under 35 U.S.C. 154(b) by 0 days.

(21) Appl. No.: 13/375,046

(22) PCT Filed: Jun. 3, 2010

(86) PCT No.: PCT/EP2010/057793
§ 371 (c)(1),
(2), (4) Date: Feb. 9, 2012

(87) PCT Pub. No.: WO2010/139767
PCT Pub. Date: Dec. 9, 2010

(65) Prior Publication Data
US 2012/0129182 A1    May 24, 2012

(30) Foreign Application Priority Data

Jun. 4, 2009    (DE) .......................... 10 2009 024 143

(51) Int. Cl.
*C12Q 1/68*    (2006.01)
(52) U.S. Cl.
CPC .................................. *C12Q 1/6851* (2013.01)
(58) Field of Classification Search
None
See application file for complete search history.

(56) References Cited

U.S. PATENT DOCUMENTS

| 2005/0069938 | A1 | 3/2005 | Wang ........................... 435/91.2 |
| 2005/0069939 | A1 | 3/2005 | Wang ........................... 435/91.2 |
| 2005/0074804 | A1 | 4/2005 | Wang ........................... 435/91.2 |
| 2005/0112639 | A1 | 5/2005 | Wang ........................... 435/91.2 |
| 2008/0128298 | A1* | 6/2008 | Bornarth et al. ............. 206/223 |

FOREIGN PATENT DOCUMENTS

| CN | 102459632 | 5/2012 |
| EP | 0623682 A1 | 11/1994 |
| EP | 0 714 987 | 6/1996 |
| EP | 0623682 B1 * | 9/1999 |
| EP | 1 484 394 | 12/2004 |
| EP | 2 438 192 | 11/2012 |
| JP | 2012513630 | 12/2011 |
| WO | WO 2010/139767 | 12/2010 |

OTHER PUBLICATIONS

Talseth-Palmer et al. Whole genome amplification and its impact on CGH array profiles. BMC Research Notes 2008;1:56-63 (listed as pp. 1-8 in the publication available).*
Venter et al. The sequence of the human genome. Science 2001;291:1304-51.*
Gibson et al. A novel method for real time quantitative RT-PCR. Genome Research 1996;6:995-1001.*
Kim et al. Amplification of uncultured single-stranded DNA viruses from rice paddy soil. Applied and Environmental Microbiology 2008; 74: 5975-5985.*
International Search Report dated Sep. 20, 2010 for PCT/EP2010/057793 filed on Jun. 3, 2010 and published as WO 2010/139767 dated Dec. 9. 2010 (Inventors: Korfhage et al. // Applicant: Qiagen Strasse) (3 pages).
Written Opinion dated Dec. 4, 2011 for PCT/EP2010/057793 filed on Jun. 3, 2010 and published as WO 2010/139767 dated Dec. 9, 2010 (Inventors: Korfhage et al. // Applicant: Qiagen Strasse) (9 pages).
International Preliminary Report on Patentability dated Dec. 6, 2011 for PCT/EP2010/057793 filed on Jun. 3, 2010 and published as WO 2010/139767 on Dec. 9, 2010 (Inventors: Korfhage et al. // Applicant: Qiagen Strasse) (10 pages).
Lage JM, et al. (2003) Whole genome analysis of genetic alterations in small DNA samples using hyperbranched strand displacement amplification and array-CGH. Genome Res. 13(2): 294-307.
Landegren U, et al. (1988) A ligase-mediated gene detection technique. Science. 241(4869): 1077-1080.
Li N, et al. (2008) CE combined with rolling circle amplification for sensitive DNA detection. Electrophoresis. 29(2): 424-432.
Liu D, et al. (1996) Rolling Circle DNA Synthesis: Small Circular Oligonucleotides as Efficient Templates for DNA Polymerases. J Am Chem Soc. 118(7): 1587-1594.
Milla MA, et al. (1998) Use of the restriction enzyme AvaI and exo-Bst polymerase in strand displacement amplification. Biotechniques. 24(3): 392-396.
Nagamine K, et al. (2001) Loop-mediated isothermal amplification reaction using a nondenatured template. Clin Chem. 47(9): 1742-1743.
Notomi T, et al. (2000) Loop-mediated isothermal amplification of DNA. Nucleic Acids Res. 28(12): E63.
Quant-iT™ PicoGreen® dsDNA Reagent and Kits—pamphlet generated by Molecular Probes // dated Aug. 26, 2010 by the International Searching Authority at http://probes.invitrogen.com/media/pis/mp07581.pdf (8 pages).
Talseth-Palmer BA, et al. (2008) Whole genome amplification and its impact on CGH array profiles. BMC Res Notes. 1: 56.
Vincent M, et al. (2004) Helicase-dependent isothermal DNA amplification. EMBO Rep. 5(8): 795-800.

(Continued)

*Primary Examiner* — Angela M Bertagna
(74) *Attorney, Agent, or Firm* — Ballard Spahr LLP

(57) ABSTRACT

What is described is a method for quantitative and qualitative analysis of complex template nucleic acids to be analyzed. The method comprises the co-amplification of a control nucleic acid with the complex template nucleic acid by means of isothermal strand displacement reaction. The method of the invention further comprises the determination of the amount of amplified control nucleic acid as measure for the determination of the quantity and/or quality of the complex template nucleic acid used. The present invention also relates to a kit for carrying out a method of the invention. Furthermore, the use of the method of the invention or the kit of the invention for standardization of whole-genome, whole-transcriptome and whole-bisulfitome analyses is described.

17 Claims, 9 Drawing Sheets

(56) References Cited

OTHER PUBLICATIONS

Wang G, et al. (2004) DNA amplification method tolerant to sample degradation. Genome Res. 14(11): 2357-2366.
Wiedmann M, et al. (1994) Ligase chain reaction (LCR)—overview and applications. PCR Methods Appl. 3(4): S51-S64.
Walker GT, et al. (1992). Strand displacement amplification—an isothermal, in vitro DNA amplification technique. Nucleic Acids Res. 20(7): 1691-1696.
Fourth Office Action dated Oct. 13, 2015 by the State Intellectual Property Office of the People's Republic of China for Chinese Patent Application No. 201080025156.5, which was filed on Jun. 3, 2010 and published as CN102459632 dated May 16, 2012 (Inventor—Korfhage et al.; Applicant—Qiagen GmbH) (21 pages).

\* cited by examiner

A

Step 1

B

C

Step 2

D

AMPLIFICATION OF COMPLEX NUCLEIC ACIDS

CROSS REFERENCE TO RELATED APPLICATIONS

The present application is a National Phase Application of International Application No. PCT/EP2010/057793, filed Jun. 3, 2010, which claims priority to German Patent Application No. 102009 024 143.4, filed Jun. 4, 2009, which applications are incorporated herein fully by this reference.

TECHNICAL FIELD OF THE INVENTION

The present invention relates to the field of biology and chemistry, in particular of molecular biology. The invention specifically relates to the amplification of complex nucleic acids, such as whole genomes, transciptomes and bisulfitomes.

BACKGROUND OF THE INVENTION

The amplification of complex template nucleic acids plays an important role in many molecular-biological applications. Thus, for some applications, it is necessary to amplify whole genomes (Whole Genome Amplification, WGA), whole transcriptomes (Whole Transciptome Amplification, WTA) or whole bisulfitomes (Whole Bisulfitomes Amplification, WBA), respectively.

Various parameters are essential for the successful amplification of such complex nucleic acids:

Suitable reaction conditions are a necessary requirement. These include, e.g., a suitable buffer with a suitable pH value and a suitable composition of monovalent and bivalent salts. However, they also include at least one suitable polymerase and suitable reaction temperatures for the amplification are essential factors for the success of the amplification.

A decisive parameter is the amount of complex template nucleic acid used. If the amount of complex template nucleic acid is too small, it will not suffice for the whole genome. For example, an amount of 6 pg human genomic DNA corresponds approximately to the haploid human genome. If less than 6 pg are used for one WGA reaction, it is not possible to completely amplify the human genome in the WGA since not all segments are represented. At the same time, an amount of less than 100 pg can also be too small since specific segments from stochastic effects are under- or overrepresented in such an amount.

A third decisive parameter for the amplification of complex template nucleic acids is the quality of the sample or the complex template nucleic acid(s) contained therein, respectively. The term "quality" may include different aspects:

The sample to be amplified containing complex template nucleic acid can have inhibitors which inhibit the polymerase used in a competitive or allosteric way or can destroy the active conformation of the polymerase. In the following, substances of this kind will be referred to as trans-inhibitors. Such trans-inhibitors include, e.g., heavy metal ions (e.g. Ni, Fe, Mn, Zn etc.), negatively charged polymers (e.g. heparin, dextran sulfate etc.) or protein-denaturing substances which are frequently used in nucleic acid preparations (e.g. SDS, phenol etc.).

However, the sample can also contain substances that bind to nucleic acids thereby inhibiting the amplification, e.g. by preventing denaturation of the nucleic acid or by preventing that the nucleic acid is recognised by a polymerase. In the following, substances of this kind will be referred to as cis-inhibitors. Such cis-inhibitors can be proteins (e.g. histones etc.), positively charged agents (e.g. positively charged polymers, positively charged amino acid etc.).

The nucleic acid can be display various defects so that, at the defect sites, an elongation reaction by the polymerase is no longer possible. These defect sites can be, e.g., single strand or double strand nicks or abasic sites or sites at which modified bases are present (e.g. modification to oxoguanin or uracil in DNA).

At present, the detection of these quantitative and qualitative properties is only possible to an insufficient degree at the beginning of a reaction for the amplification of complex template nucleic acids. It is often not clear in which quality or amount of the complex nucleic acid to be amplified is present. Thus, with very small amounts of complex template nucleic acid, the measurement of concentration cannot be carried out by OD260 measuring. DNA damages can only be determined by gel electrophoresis if the DNA amount is so ample that gel electrophoresis can be carried out. At present it is not possible to determine other damages, such as e.g. abasic DNA segments.

Control of these qualitative parameters of the complex template nucleic acid e.g. via quantitative PCR can be only carried out in an unsatisfactory manner since quantitative PCR allows only poor detection of differences in size for partially degraded DNA if the template nucleic acid has an average size of >1 kb. However, such differences in size can be crucial for the amplification of a complex nucleic acid.

DESCRIPTION OF THE INVENTION

Figure 1A:
FIG. 1: Schematic illustration of the claimed method. In step 1 the control nucleic acid (A), complex template nucleic acid (B) and primers are provided. In step 2 the co-amplification of control (C) and complex template nucleic acid (D) takes place. After completion of the co-amplification of the control nucleic acid (E) and complex template nucleic acid (F), the amount of amplified control nucleic acid for the known sequence segment (dotted line) is determined in step 3.
Figure 1B:
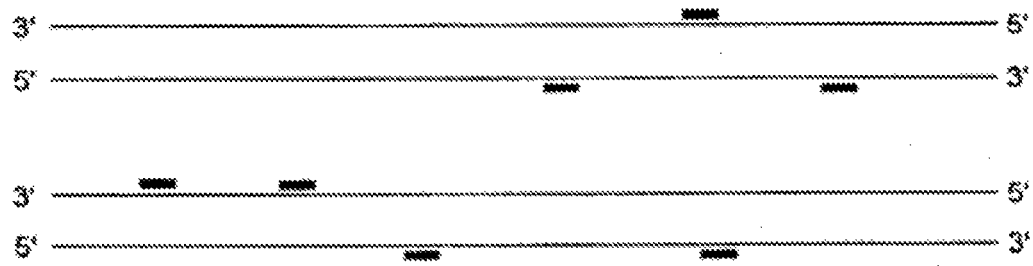
Figure 1C:
Figure 1D:
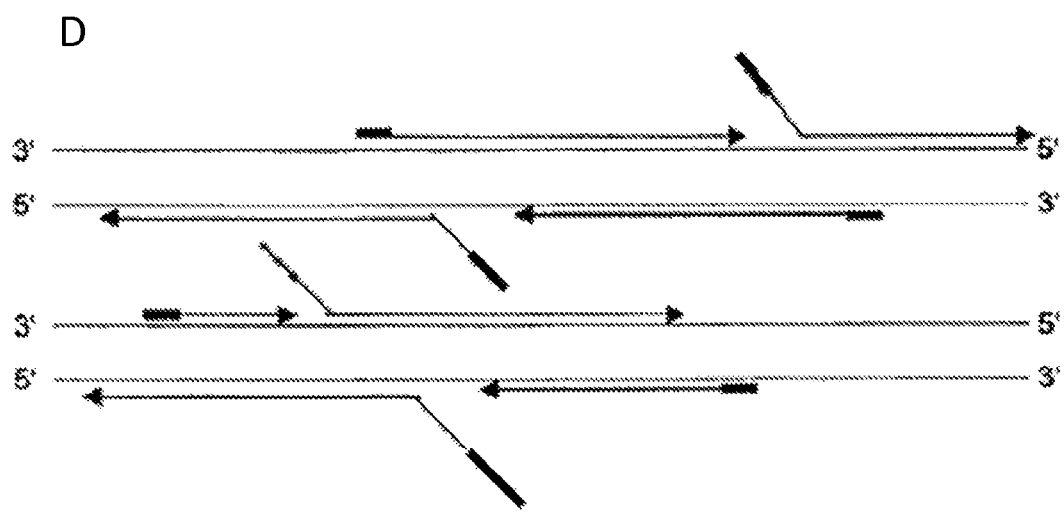
Figure 1E:
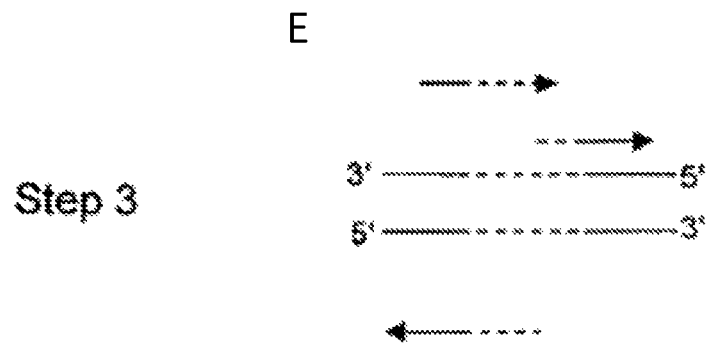
Figure 1F:
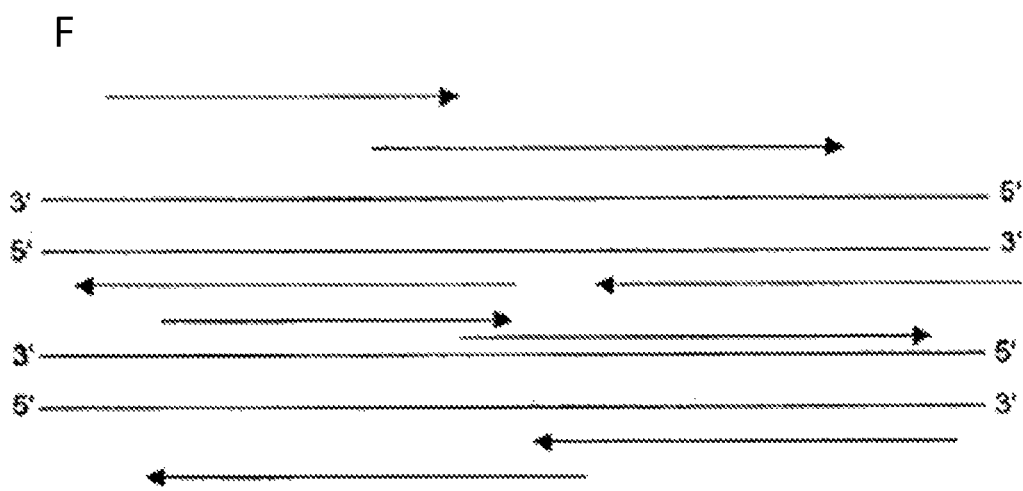

Thus, the present invention relates to a method for quantitative and qualitative analysis of one or more complex template nucleic acids, that are to be amplified, in a sample comprising the following steps:
providing a reaction mixture comprising
the complex template nucleic acid to be amplified,
a specified amount of at least one control nucleic acid, wherein the control nucleic acid has less than 50% sequence identity with the template nucleic acid and wherein said control nucleic acid has at least one known sequence segment,
primer for amplification of the template nucleic acid,
primer for amplification of the control nucleic acid, and
enzymes and reagents suited for the amplification of nucleic acids;
co-amplification of the template nucleic acid and the control nucleic acid, wherein the co-amplification takes place isothermally, wherein the co-amplification comprises a strand displacement reaction and wherein template and control nucleic acid essentially are amplified completely in said amplification;
after completion of the co-amplification, the amplified control nucleic acid is quantified.

Thus, in the present invention, one or more exogenous control nucleic acids are added to the reaction mixture for amplification of one or more complex template nucleic acids. After the addition of primers and reagents and enzymes suited for the amplification of the complex template nucleic acid and/or the control nucleic acid, a co-amplification of the complex template and control nucleic acids is carried out. Thus, the control nucleic acid is amplified in parallel to the complex template nucleic acid. The degree of the amplification of the control nucleic acid depends on the presence, the quantity and the quality of the complex template nucleic acid. Thus, the control is a competitive control since the control nucleic acid and the template nucleic acid compete for the resources of the amplifications reaction, such as primers, dNTPs, polymerase. After completion of the co-amplification, the amplified control nucleic acid(s) are quantified. The quantity determined in this way allows to draw conclusions regarding the starting amount or quality of the complex template nucleic acid, respectively. A small quantity of control nucleic acid after amplification correlates with sufficient quantity and quality of complex template nucleic acid used. Accordingly, lack of quantity or quality of the complex nucleic acid used can be inferred from a greater amount of amplified control nucleic acid.

Moreover, the determination of the relative quantity of control nucleic acid in the mixture of amplified nucleic acids allows to infer the reaction conditions regarding pH value, buffer, salt concentration or polymerase activity.

In one embodiment, the total amount of amplified nucleic acid is determined after completion of the co-amplification in addition to the determined amount of amplified control nucleic acid. If the relative quantity of amplified control nucleic acid determined in this way is high, this is correlated, according to the invention, with suitable reaction conditions for the amplification. If the total amount of amplified nucleic acid is low and the quantity of amplified control nucleic acid is also low, this is an indicator for amplification reaction conditions that are not suited.

The present method can also be used to test reaction conditions and/or the activity of polymerases. This is particularly the case if no template nucleic acid but exclusively the control nucleic acid is used.

The control nucleic acid used according to the invention has at least one segment of defined sequence which at least one sequence specific probe and/or one or more primers hybridise with. According to the invention, the control nucleic acid has less than 50% sequence identity with the complex template nucleic acid over the total length of the control nucleic acid, preferably less than 65%, particularly preferred less than 80%. According to the invention, the sequence identity between two sequences is determined using the mathematical algorithm of Karlin and Altschul (1983) *Proc. Natl. Acad. Sci. USA* 90: 5873-5877.

Furthermore, in the context of the present invention, a linear control nucleic acid comprises a length of at least 800 nucleotides, preferably more than 1,000 and less than 80,000 nucleotides, particularly preferred more than 5,000 and less than 50,000 nucleotides. The control nucleic acid can be of natural origin, i.e. isolated from organisms such as e.g. phages, viruses, bacteria or eukaryotic organisms. However, according to the invention, it can also have a sequence that does not occur naturally. To the person skilled in the art, it is obvious that a combination of naturally occurring and not naturally occurring sequences can also serve as control nucleic acid. The control nucleic acid can consist of DNA or RNA and be single-stranded as well as double-stranded.

In a preferred embodiment of the invention, the lambda-phage genome is used as control nucleic acid. The use of one or more fragments of the lambda-phage genomes is particularly preferred. Fragments can, for example, be generated by digestion of the nucleic acid using nucleases. The person skilled in the art knows that such nucleases can also be sequence-specific restriction endonucleases.

In another preferred embodiment of the invention, the control nucleic acid is present in circular form. The person skilled in the art knows that such circular control nucleic acid can have different origins. Thus, the circular nucleic acid may be derived from viruses, phages, microorganisms (unicellular organisms) but also pluricellular organisms. A circular control nucleic acid of the invention can comprise less than 800 nt. In a preferred embodiment of the invention, the circular control nucleic acid, however, comprises more than 50 nt, particularly preferred more than 100 nt.

According to the invention, the complex template nucleic acid to be analysed comprises more than 10,000 nucleotides, preferably between 100,000 and 1,000,000 nucleotides, particularly preferred more than 1,000,000 nucleotides.

The complex template nucleic acid is preferably DNA or RNA. For example, it can be nucleic acid selected from the group consisting of cDNA (complementary DNA), LNA (locked nucleic acid), mRNA (messenger RNA), mtRNA (mitochondrial RNA), rRNA (ribosomal RNA), tRNA (transfer RNA), nRNA (nuclear RNA), dsRNA (double-stranded RNA), ribozyme, riboswitch, viral RNA, dsDNA (double-stranded DNA), ssDNA (single-stranded DNA), plasmid DNA, cosmid DNA, chromosomal DNA, viral DNA, mtDNA (mitochondrial DNA), nDNA (nuclear DNA). Furthermore, the complex template nucleic acid can also be the entirety of a group of nucleic acids, preferably the entirety of mRNA or cDNA (transcriptome), respectively, and/or the entirety of DNA (genome) of one or more organisms. The person skilled in the art knows that the entirety of RNA can represent the genome of an organism, which, in particular, applies to RNA viruses. The complex template nucleic acid can also consist of one or more chromosomes. The complex template nucleic acid can be present in fragmented or non-fragmented form. It can also be fragmented prior to amplification by means of enzymatic, physical or chemical methods. A bisulfitome of the invention is a complex DNA, wherein non-methylated cytosine bases have been transformed into uracil bases using a bisulfate treatment.

In a preferred embodiment of the method of the invention, the complex template nucleic acid to be analysed is a template nucleic acid in a WGA and/or WTA and/or WBA.

The complex template nucleic acid to be analysed can have different origins. For example, it can have been isolated from one or more organisms selected from the group consisting of viruses, phages, bacteria, eukaryotes, plants, fungi and animals. Furthermore, the complex template nucleic acid to be analysed can be part of samples. Such samples can also be of various origins. Thus, the method of the invention also relates to the analysis of complex template nucleic acids contained in environmental samples.

The method of the invention can also require a lysis of the organism, containing the complex template nucleic acid, prior to amplification. In the context of the present invention, the term 'lysis' refers to a process which leads to the release of nucleic acids and/or proteins from a sample material into the environment. It is possible that the structure of the sample material is destroyed during this process, e.g. the envelope of the sample material can be dissolved. In the context of the present invention, the term "lysis" also refers to the fact that the complex template nucleic acid can be discharged from the sample material via small openings, e.g. pores etc. in the envelope/coat of the sample material without destroying the structure of the sample material. It is, for example, possible to create pores using lysis reagents. In the context of the present invention, the term "lysis" further refers to the fact that nucleic acids and/or proteins of the sample material, which seems to be already destroyed in its structure or has small openings, can be washed out using an additive. The lysis results in a lysate. The lysate can contain sample material from different organisms or from a single organism.

In the context of the invention, amplification is understood to be the multiplication of one or more nucleic acids by the factor 2. For this purpose, the nucleic acid can be multiplied in a linear or in an exponential manner. By exponential amplification methods, the nucleic acid is multiplied to a higher degree than by factor 2. Other enzymatic methods can also be used, these may be selected from the group comprising the "rolling circle amplification" (as described in Liu et al., "Rolling circle DNA synthesis: Small circular oligonucleotides as efficient templates for DNA polymerases", J. Am. Chem. Soc. 118:1587-1594 (1996)), the "isothermal amplification" (as described in Walker et al., "Strand displacement amplification—an isothermal, in vitro DNA amplification technique", Nucleic Acids Res. 20(7): 1691-6 (1992), the "ligase chain reaction" (as described in Landegren et al., "A Ligase-Mediated Gene Detection Technique," Science 241:1077-1080, 1988, or in Wiedmann et al., "Ligase Chain Reaction (LCR)—Overview and Applications", PCR Methods and Applications (Cold Spring Harbor Laboratory Press, Cold Spring Harbor Laboratory, NY, (1994) S. S51-S64)).

According to the invention, said amplification can be combined with various different methods and reactions. The person skilled in the art is familiar with relevant nucleic acid modifying methods, e.g. reverse transcription, ligation, nucleic acid fill-in reactions, terminal template-independent additions, digestion with restriction endonulcease and/or the treatment with so-called nicking enzymes. Moreover, helicases and/or single-strand binding proteins (e.g. SSB, T4gp32, rec A etc.) can also be used.

Linear amplification is achieved, for example, by means of "rolling circle amplification" (RCA) in the presence of primers which hybridise on the target circle with only one specific sequence. Exponential amplification is achieved, for example, via RCA with primers, wherein the primers hybridise with at least two binding sites on the target circle or with at least one binding site on the target circle and at least one binding site on the complementary strand. Further linear and exponential amplification methods that are suited for the present invention, such as MDA or PCR, are known to the person skilled in the art.

The amplification reaction used in the context of the present invention is preferably an isothermal strand displacement reaction (as described in Walker et al., "Strand displacement amplification—an isothermal, in vitro DNA amplification technique", Nucleic Acids Res. 20(7):1691-6 (1992)) for co-amplification of complex template nucleic acid and control nucleic acid. Strand displacement reaction herein refers to any reaction in which a polymerase having strand displacement activity is used or in which a reaction condition allowing strand displacement is used. These include e.g. the strand displacement amplification (SDA) as well as the multiple displacement amplification (MDA) or the rolling circle amplification (RCA) and all sub-types of this reaction, such as e.g. restriction-aided RCA (RCA-RCA) or MDA with nested primers, linear and exponential strand displacement reactions or helicase-dependent amplification (EP 20050112639; EP 20050074804; EP 20050069939; EP 20050069938; Wang G. et al. (2004), DNA amplification method tolerant to sample degradation, Genome Res. November; 14(11):2357-2366; Mila M. A. et al., (1998), Use of the restriction enzyme AvaI and exo-Bst polymerase in strand displacement amplification; Biotechniques March; 24(3):392-396; Nagamine K. et al., (2001), Loop-mediated isothermal amplification reaction using a nondenatured template. Clin. Chem. 47(9):1742-1743; Notomi et al. (2000), Loop-mediated isothermal amplification of DNA, Nucleic Acids Res. 28(12):E63; Lage J. M. et al. (2003), Whole genome analysis of genetic alterations in small DNA samples using hyperbranched strand displacement amplification and array-CGH, Genome Res. 13(2): 294-307; and Vincent M. Xu Y., Kong H. (2004), Helicase-dependent isothermal DNA amplification, EMBO Rep. 5(8): 795-800).

An isothermal reaction of the invention is understood to be a reaction which is carried out only at one temperature. If the temperature of the reaction is changed prior to the begin of the reaction (e.g. on ice) or after completion of the reaction (e.g. in order to inactivate reaction components or enzymes), the reaction is still referred to as isothermal, as long as the reaction per se is carried out at a constant temperature. The temperature is considered to be constant if the temperature variations do not exceed +/−10° C.

According to the invention, strand displacement activity of a polymerase means that the enzyme used is capable of cleaving a double-strand of a nucleic acid into two single-strands. In most of the cases, RNA polymerases have strand-displacement activity. A known example is T7 RNA polymerase. Further examples are known to the person skilled in the art. DNA polymerases with strand displacement activity which can be used, for example, in the RCA are e.g. holoenzymes or portions of replicases from viruses, prokaryotes, eukaryotes or archeae, Phi 29-like DNA polymerases, the DNA polymerase Klenow exo- from *Bacillus stearothermophilus* with the designation Bst exo-. "exo-" means that the relevant enzyme does not have 5'-3' exonuclease activity. A known representative of the Phi 29-like DNA polymerases is the DNA polymerase from the bacteriophage Phi 29. Other Phi 29-like DNA polymerases occur, for example, in the phages Cp-1, PRD-1, Phi 15, Phi 21, PZE, PZA, Nf, M2Y, B103, SF5, GA-1, Cp-5, Cp-7, PR4, PR5, PR722 and L 17. Further suitable DNA polymerases with strand displacement activity are known to the person skilled in the art. Alternatively, DNA polymerases with strand displacement activity are also understood to include DNA polymerases without strand displacement activity if, in addition to a relevant DNA polymerase, a catalysator is used, for example a protein or ribozyme, which allows the cleavage of a DNA double-strand or the stabilisation of DNA single-strands. These proteins include, for example, the helicases, SSB proteins and recombination proteins which can be contained as part of larger enzyme complexes such as e.g. replicases. In this case, additional components apart from the polymerase lead to the creation of a polymerase with strand displacement activity. The polymerases with strand displacement activity may be heat-instable or heat-stable.

In a preferred embodiment, the polymerase with strand displacement activity used for co-amplification is a Ph 29-like polymerase, preferably a polymerase from a phage selected from a group of phages comprising Phi 29, Cp-1, PRD-1, Phi 15, Phi 21, PZE, PZA, Nf, M2Y, B103, SF5, GA-1, Cp-5, Cp-7, PR4, PR5, PR722 and L 17. The use of the polymerase from phage Phi 29 is particularly preferred.

It is obvious to the person skilled in the art that it is also possible to use combinations of two or more polymerases with stand displacement activity. Furthermore, one or more polymerases with stand displacement activity can be combined with one or more polymerases without stand displacement activity.

In a preferred embodiment of the method of the invention, the primers used for amplification of the complex template nucleic acid are also used for the amplification of the control nucleic acid.

A primer within the meaning of the present invention is understood to be a molecule which serves as starting site for an enzyme with nucleic acid polymerase activity. This primer can be a protein, a nucleic acid or another molecule which the skilled person considers a suitable polymerase starting site. The molecule functions as starting site on the basis of intermolecular as well as intermolecular interaction. Nucleic acid primers do not necessarily, but may, hybridise over their whole length with the template nucleic acid.

The use of random primers is particularly preferred for the co-amplification of control nucleic acids and complex template nucleic acids, i.e. a primer mixture comprising a number of different primers with random sequence.

Apart from random primers, also other primers can be used for the amplification of the template nucleic acid or the control nucleic acid, respectively. Thus, also degenerate and/or sequence specific primers can be used for the amplification of control nucleic acid and/or template nucleic acid.

The primers used for amplification comprise 4 to 25 bases, preferably between 5 to 15 bases, particularly preferred 6 to 10 bases.

In the method of the invention, the quantification of the amplified control nucleic acid is carried out for the at least one known sequence segment. Quantification by means of quantitative (real time) PCR (qRT-PCR) by amplifying of a portion or the entire control nucleic acid using sequence-specific primers which hybridise with the at least one known sequence segment.

In a preferred embodiment, the lambda-phage DNA or fragments thereof are used also control nucleic acid. In this embodiment of the method of the invention, the control nucleic acid is quantified by qRT-PCR, preferably using sequence-specific primers. In a particularly preferred embodiment, primers of sequence SEQ ID NO:1 or SEQ ID NO:2, respectively.

The DNA polymerase that is used during quantitative (real time) PCR preferably is a polymerase from a thermophilic organism or a thermostable polymerase or a polymerase selected from the group of *Thermus thermophilus* (Tth) DNA polymerase, *Thermus acquaticus* (Taq) DNA polymerase, *Thermotoga maritima* (Tma) DNA polymerase, *Thermococcus litoralis* (Tli) DNA polymerase, *Pyrococcus furiosus* (Pfu) DNA polymerase, *Pyrococcus woesei* (Pwo) DNA polymerase, *Pyrococcus kodakaraensis* KOD DNA polymerase, *Thermus filiformis* (Tfi) DNA polymerase, *Sulfolobus solfataricus* Dpo4 DNA polymerase, *Thermus pacificus* (Tpac) DNA polymerase, *Thermus eggertsonii* (Teg) DNA polymerase, *Thermus brockianus* (Tbr) and *Thermus flavus* (Tfl) DNA polymerase.

In the case of RNA, for example mRNA, the RNA must be reverse transcribed into DNA. This is done using an enzyme with reverse transcriptase activity. Enzymes of this kind can be, for example, reverse transcriptases from viruses, bacteria, archae bacteria and eukaryotes, in particular from thermostable organisms. These also include, e.g., enzymes from introns, retro-transposons or retroviruses. An enzyme with reverse transcriptase activity of the invention is an enzyme that, under suitable buffer conditions, is capable of incorporating in a complementary manner desoxyribonucleotides into the ribonucleic acid at the 3'-end of a desoxyoligonucleotide or ribooligonucleotide hybridized to the ribonucleic acid. This includes, on the one hand, enzymes having this natural function but, one the other, also enzymes that get this function only by the modification of their gene sequence, such as e.g. mutagenesis or appropriate buffer conditions.

The enzyme with reverse transcriptase activity is preferred to be an enzyme selected from the group comprising HIV reverse transcriptase, M-MLV reverse transcriptase, EAIV reverse transcriptase, AMV reverse transcriptase, *Thermus thermophilus* DNA polymerase I, M-MLV RNAse H, Superscript®, SuperScript® II, SuperScript® III, Monsterscript™ (Epicentre), Omniscript, SensiScript® reverse transcriptase (Qiagen), ThermoScript™ and Thermo-X (both Invitrogen). According to the invention, it is also possible to use enzymes which exhibit reverse transcriptase only after a modification of the gene sequence. It is also possible to use a reverse transcriptase activity with increased accuracy regarding the error rate. AccuScript™ reverse transcriptase (Stratagene) is an example of reverse transcriptases of this kind. To the person skilled in the art, it is obvious that it is also possible to use mixtures of two or more enzymes with reverse transcriptase activity.

The person skilled in the art knows that most enzymes with reverse transcriptase activity require a divalent ion. Thus, in a preferred embodiment, those enzymes requiring a divalent ion include a divalent ion. $Mg^{2+}$, $Mn^{2+}$ are preferred.

Preferred combinations of enzymes are HIV reverse transcriptase or M-MLV reverse transcriptase or EAIV reverse transcriptase or AMV reverse transcriptase or *Thermus thermophilus* DNA polymerase I or M-MLV RNAse H minus, Superscript, SuperScript II, SuperScript III or Monsterscript™ (Epicentre) or Omniscript reverse transcriptase (Qiagen) or SensiScript® reverse transcriptase (Qiagen), ThermoScript™, Thermo-X (both Invitrogen) or a mixture of two or more enzymes with reverse transciptase activity and poly-(A)-polymerase from *Escherichia coli*. In addition, HIV reverse transcriptase or M-MLV reverse transcriptase or EAIV reverse transcriptase or AMV reverse transcriptase or *Thermus thermophilus* DNA polymerase I or M-MLV RNAse H minus, Superscript, SuperScript II, SuperScript III or Monsterscript™ (Epicentre) or Omniscript reverse transcriptase (Qiagen) or SensiScript® reverse transcriptase (Qiagen), ThermoScript™, Thermo-X (both Invitrogen) or a mixture of two or more enzymes with reverse transciptase activity and poly-(A)-polymerase from yeast.

In the qRT-PCR, fluorescent-labelled primers and/or probes can be used, e.g. LightCycler® probes (Roche), TaqMan® probes (Roche), molecular beacons, Scorpion primers, Sunrise primers, LUX™ primers or amplifluor primers. Probes and/or primers can contain e.g. covalently or non-covalently bound fluorescent dyes such as for example fluorescein isothiocyanate (FITC), 6-carboxyfluorescein (FAM), xanthene, rhodamine, 6-carboxy-2',4',7',4,7-hexachlorofluoresceine (HEX), 6-carboxy-4',5'-dichloro-2',7'-dimethodyfluoresceine (JOE), N,N,N',N'-tetramethyl-6-carboxyrhodamine (TAMRA), 6-carboxy-X-rhodamine (ROX), 5-carboxyrhodamine-6G (R6G5), 6-carboxyrhodamine-6G (RG6), rhodamine 110; coumarines such as umbelliferones, benzimides such as Hoechst 33258; phenanthridines such as Texas Red, ethidiumbromides, acridine dyes, carbazole dyes, phenoxazine dyes, porphyrine dyes, polymethine dyes, cyanine dyes such as Cy3, Cy5, Cy7, SYBR® Green, BODIPY® dyes, quinoline dyes and alexa dyes.

The person skilled in the art knows that, in qRT-PCR, double-strand-specific fluorescent dyes, e.g. ethidiumbromide, SYBR® Green, PicoGreen®, RiboGreen® etc., can be used independently of primers and probes.

The person skilled in the art knows which conditions are suited for quantitative PCR or quantitative reverse transcriptase PCR. This applies, for example, to primer design, the selection of suitable processing temperatures (reverse transcription, denaturing, primer annealing, elongation), the number of PCR cycles, buffer conditions, reverse transcriptase and the evaluation of quantitative (real time) PCR.

According to the invention, low Ct (threshold cycle) values for one or more amplicon(s) of the control nucleic acid as determined by qRT-PCR are correlated with low quality and/or low quantity of the complex template nucleic acid. Accordingly, high Ct values indicate high quality and/or quantity of the complex template nucleic acid.

In a preferred embodiment of the invention, the quality and/or quantity of the complex template nucleic acid to be amplified is determined by means of the delta Ct value. Said delta Ct value is calculated based on the difference between the Ct value determined for the control nucleic acid after co-amplification with the complex template nucleic acid and the Ct value of the control nucleic acid in a control reaction. The control reaction is characterised in that no complex template nucleic acid is added. However, the other elements as well as the reaction conditions remain unchanged. The higher the delta Ct value of the amplicons of the control nucleic acid after amplification of the complex nucleic acid, the higher the quality of the complex nucleic acid used for the amplification.

The present invention also relates to a kit for carrying out the method described above, comprising:
  random primers or sequence-specific primers for the amplification of the control nucleic acid and the complex template nucleic acid,
  one or more control nucleic acids wherein the control nucleic acids have at least one known sequence segment each,
  a DNA polymerase with strand displacement activity.

Optionally, the kit of the invention can contain further components, e.g.
  a buffer solution or a buffer stock solution,
  dNTPs (preferably as solution of a mixture of dCTP, cATP, dGTP and DTTP (e.g. 5 mM of each, "dNTP mix")),
  a thermostable polymerase,
  at least one double-strand-specific fluorescent dye,
  optionally, a buffer solution or a buffer stock solution,
  enzymes and reagents for carrying out a qRT-PCR and/or
  one or more primer pairs and/or sequence-specific probes wherein the primers and/or the sequence-specific probe are capable of hybridizing within the known sequence segment of the control nucleic acid and are suited to quantify the control nucleic acid.

A kit of the invention can also contain instructions for carrying out the above-described method.

Apart from the quantity and/or quality of the complex template nucleic acid, the level of the Ct values of the amplicons of the control nucleic acid depends to a decisive degree on the amount of control nucleic acid used and the reaction conditions of the amplification. In order to have the possibility of comparing WGA, WTA and/or WBA that were not carried out simultaneously, it is desirable to provide standardised conditions. However, this is not always possible in every respect. In order to compare reactions that were conducted at different times and/or at different places with possibly different conditions, for example, internal standards of the reactions are necessary. To the person skilled in the art, it is obvious that the methods of the invention and/or kits are suited to be used as standards of this kind in WGA and/or WTA and/or WBA.

Thus, the invention also relates to the use of one of the above-mentioned methods or of the kit of the invention for the standardisation of WGA and/or WTA and/or WBA. According to the invention, the use of delta Ct values determined for the standardisation of WGA and/or WTA and/or WBA is particularly preferred.

Sequences

| SEQ ID NO. | Sequence | Use |
|---|---|---|
| SEQ ID NO. 1 | 5'-GAGACGCTGGAGTACAAACG-3' | Forward primer for marker standard 1 of the control nucleic acid |

-continued

| SEQ ID NO. | Sequence | Use |
|---|---|---|
| SEQ ID NO. 2 | 5'-CCAGCGGATTATCGCCATACTG-3' | Reverse primer for marker standard 1 of the control nucleic acid |
| SEQ ID NO. 3 | 5'-TGCTCCCTGTCCCATCTG-3' | Forward primer for marker 699 |
| SEQ ID NO. 4 | 5'-AGACAGTATGCCTTTATTTCACCC-3' | Reverse primer for marker 699 |
| SEQ ID NO. 5 | 5'-GTCTTTAGCTGCTGAGGAAATG-3' | Forward primer for marker 1004 |
| SEQ ID NO. 6 | 5'-AGCAGAATTCTGCACATGACG-3' | Reverse primer for marker 1004 |
| SEQ ID NO. 7 | 5'-AGTGCTAATGTCATGTCTCTT-3' | Forward primer for marker HexA |
| SEQ ID NO. 8 | 5'-GCTGAGAGGAGTGGAAGCT-3' | Reverse primer for marker HexA |
| SEQ ID NO. 9 | 5'-AGTGCTAATGTCATGTCTCTT-3' | Forward primer for marker HexG |
| SEQ ID NO. 10 | 5'-GCTGAGAGGAGTGGAAGCC-3' | Reverse primer for marker HexG |

EXAMPLES

Example 1

Method for the determination of the amount of template nucleic acid, which was used for the WGA using control nucleic acids in WGA reactions.

Background: The representation of the control nucleic acid in the WGA DNA after the whole-genome amplification of template nucleic acid and control nucleic acid can be indicative of the amount of the template nucleic acid used originally.

Different amount of human genomic DNA (0; 1.5; 3.125; 6.25; 12.5; 25; 50 or 100 ng) were used in a whole-genome amplification (WGA) reaction. The WGA reaction was carried out with REPLI-g® reagents according to the manufacturer's instructions (Qiagen). 20 pg of a lambda DNA was added to the individual WGA reactions as control nucleic acid, wherein contrary to the template nucleic acid, the control nucleic acid was not denatured. After the WGA reaction, the concentration and yield of total GNA was determined by means of PicoGreen® reagent (see REPLI-g® manual) (FIG. 1).

The representation of the control nucleic acid and the template nucleic acid was analysed by means of quantitative real time PCR. For this purpose, 10 ng of the resulting total DNA were used in a quantitative real time PCR (Quanti-Tect® real time PCR SYBR® Green; Qiagen). In this context, the Ct value (threshold cycle) of the control nucleic acid is given as the measure for representative amplification of complex template DNA. The Ct value shows the PCR cycle by means of which the fluorescence above the basic fluorescence can be detected for the first time. Low representation of the markers would lead to high Ct values, high representation would lead to low Ct values. If representation remains the same with different solutions, no change of the Ct value is observed. A Ct value of approximately 40 cycles shows that the analysed marker is not present in the analysed solution.

For the analysis of the representation of complex template nucleic acids after completed WGA reaction, markers 699 and marker 1004, which were contained in the template DNA used, were quantified in quantitative real time PCR reactions. For the analysis of the representation of the control nucleic acid after WGA, the marker standard 1, which is contained therein, was used. In this context too, 10 ng of the amplified total DNA were used each time. QuantiTect real time PCR SYBR® Green reagents (QIAGEN) were used as real time PCR reagents according to the manufacturer's instructions. Oligonucleotides of SEQ ID NO:3 and SEQ ID NO:4 were used as primer for marker 699. Oligonucleotides of SEQ ID NO:5 and SEQ ID NO:6 were used as primer for marker 1004. Oligonucleotides of SEQ ID NO:1 and SEQ ID NO:2 were used as primer for the marker standard 1 of the control nucleic acid.

Figure 2:
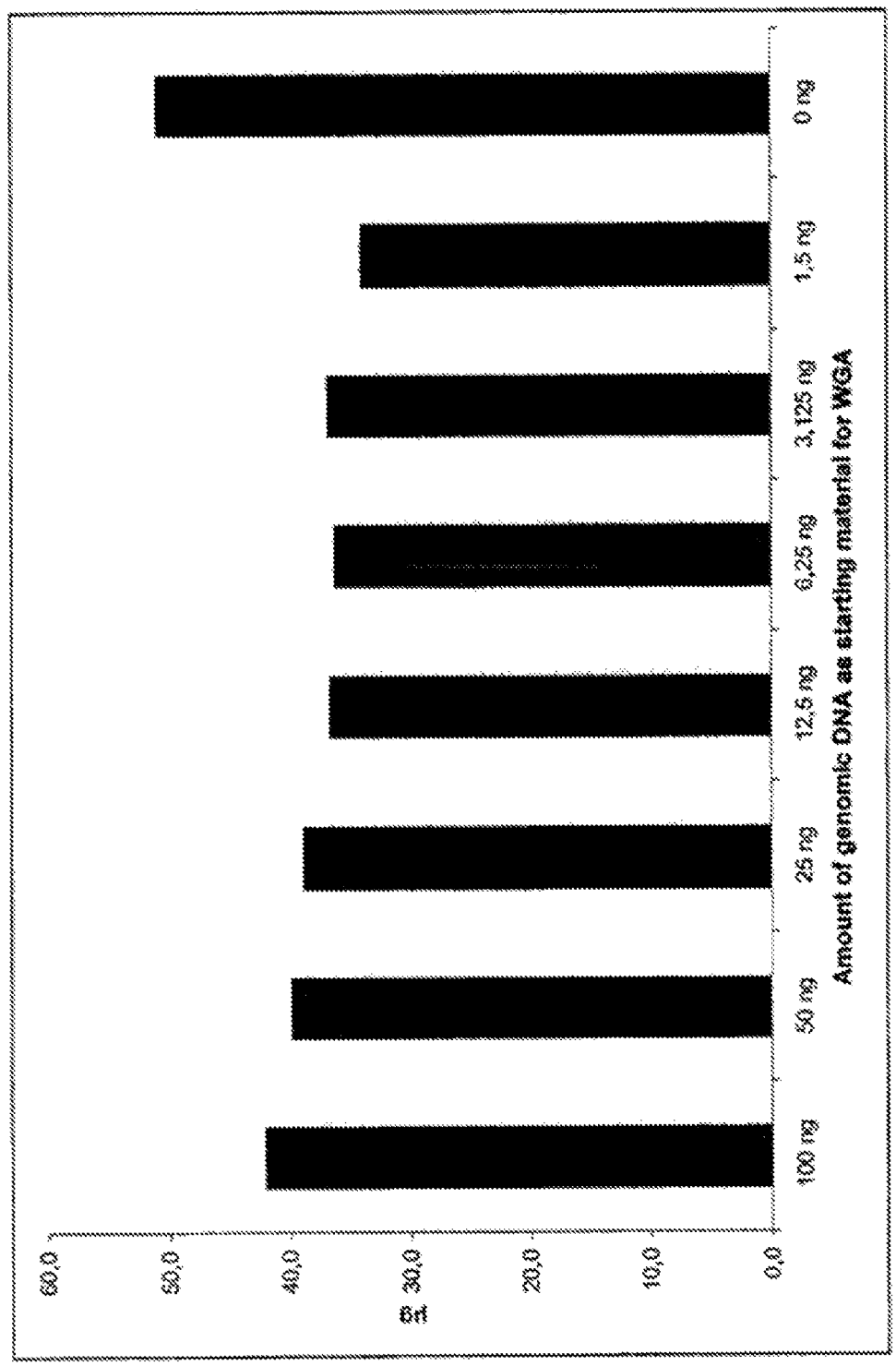
FIG. 2: Yield of total DNA after completion of whole-genome amplification: for the WGA, a mixture of control DNA (20 pg) and different amounts of template nucleic acid (0-100 ng) are used.

Result: The measurement of the yield of total DNA after completed whole genome amplification reactions showed only a slight decrease in amplified total DNA depending on the amount of template nucleic acid used (1.56 ng to 100 ng; FIG. 2).

Figure 3:
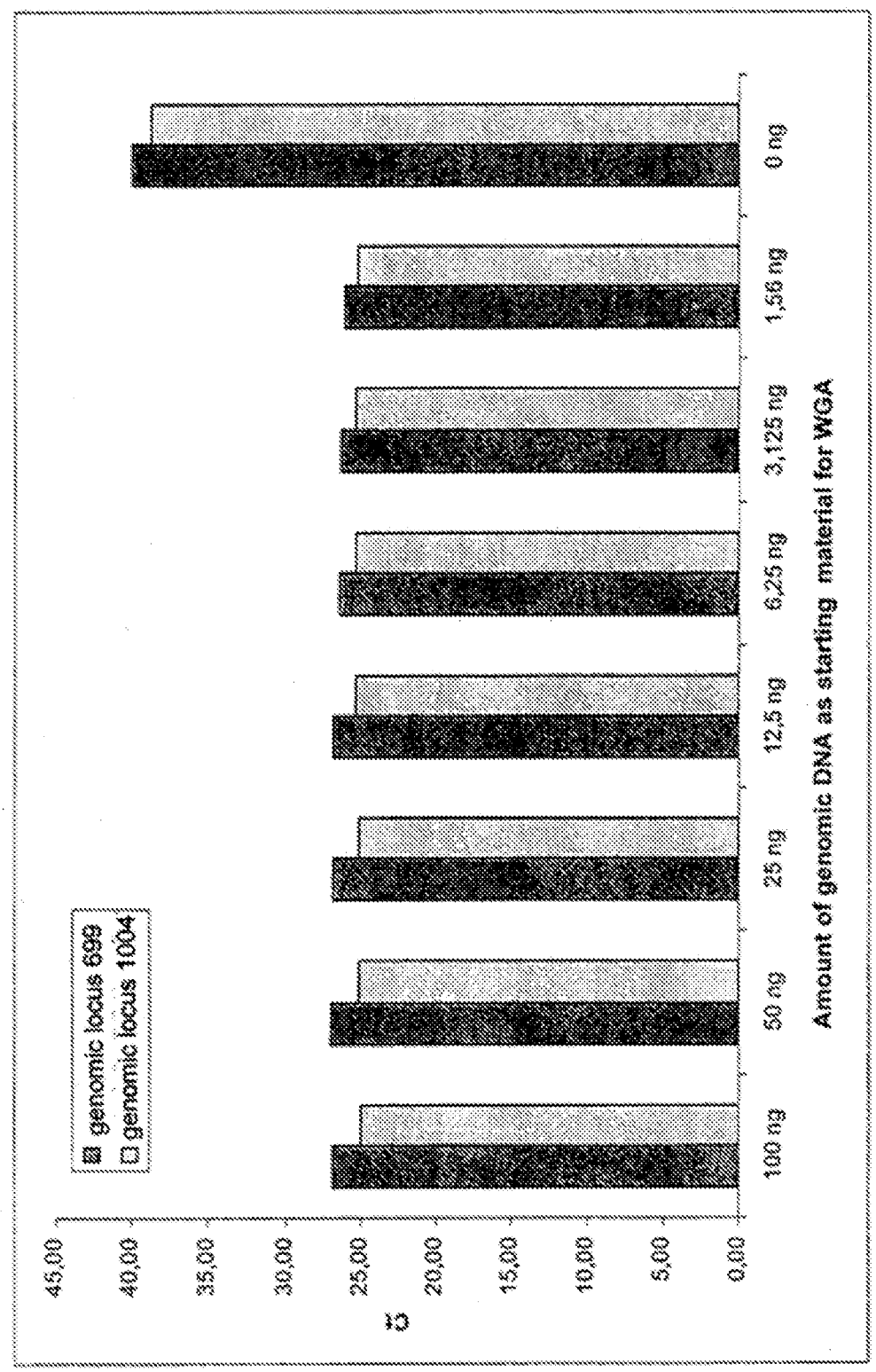
FIG. 3: Representation of the template nucleic acid marker 699 and 1004 in 10 ng WGA DNA. On the Y axis the Ct value from the real time PCR analysis is illustrated. There was no correlation between the Ct value and the amount of template nucleic acid for the WGA reaction.

For the analysis of the representation of the template nucleic acid marker 699 and 1004 in the amplified total DNA, 10 ng were used in the qRT-PCR for the various WGA solutions each. The analysis showed no correlation of the Ct value with the amount of complex template nucleic acid starting material used in the WGA. Despite different amounts of template nucleic acid, during real time PCR analysis, the Ct value remained constant for the WGA (FIG. 3).

Figure 4:
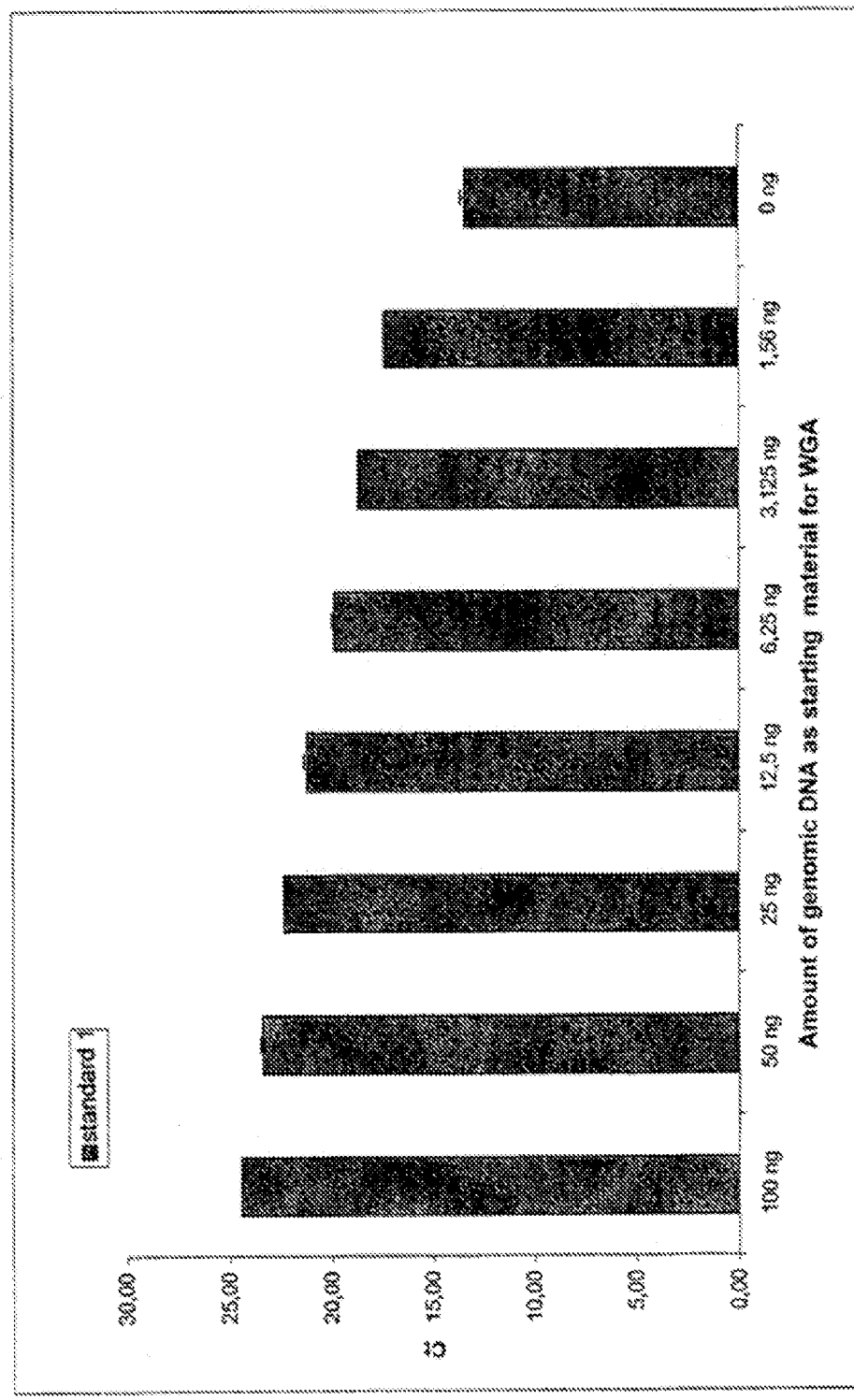
FIG. 4: Representation of the control nucleic acid marker standard 1 in 10 ng WGA DNA. On the Y axis the Ct value from the real time PCR analysis is illustrated. There was a clear correlation between the Ct value and the amount of template nucleic acid for the WGA reaction.

When 10 ng of WGA total DNA was used for the analysis of the representation of the control nucleic acid in a real time PCR, however, a strong correlation of the Ct value with the original starting amount of template nucleic acid was determined for WGA reactions: the smaller the starting amount of template nucleic acid for the WGA, the lower the Ct value of the marker standard 1 representing the control nucleic acid (FIG. 4).

Example 2

Method for the determination of the quality/integrity of the complex template nucleic acid used for the WGA while using a control nucleic acid.

Background: The representation of the control nucleic acid in the total DNA after the WGA of complex template nucleic acid and control nucleic acid can be indicative for the quality/integrity of the originally used complex template nucleic acid.

Experiment: Genomic DNA is damaged by partial digestion with the restriction endonuclease HaeIII. For this purpose, 20 μg human genomic DNA is incubated in a 200 μl solution with 1.9 U HaeIII for 0, 5, 10, 20, 40, and 80 minutes at 37° C. The resulting progressive cleavage of the DNA by HaeIII represents different degradation degrees of the complex template nucleic acid and, thus, represents different quality/integrity levels of the complex template nucleic acid. 10 ng of the thus obtained template nucleic acid with different degradation degree was in combination with 20 pg control DNA in a WGA. The WGA reaction was carried out with REPLI-g® reagents according to the REPLI-g® manufacturer's instructions (Qiagen), wherein contrary to the template nucleic acid, the control nucleic acid was not denatured. After completion of the WAG, the concentration and yield of DNA was determined by means of the PicoGreen® Reagent (see REPLI-g® manual).

The representation of the control DNA and the complex template DNA was analysed in qRT PCR. For this purpose, 10 ng of the total DNA formed in the WGA were used in a real time PCR (QuantiTect® real time PCR SYBR® Green Reagents, Qiagen). For the analysis of the representation of the complex template nucleic acid after completed WGA, the markers 699 and 1004 were used in the DNA, which was amplified in the WGA, in qRT PCR. For the analysis of the representation of the control nucleic acid after completed WGA, the marker standard 1 was used. For this purpose, too, 10 ng of the amplified total DNA was used each time. The QuantiTect® real time PCR SYBR® Green Reagents (Qiagen) were used as qRT-PCR reagents. Olgionucleotides of SEQ ID NO:2 and SEQ ID NO:3 were used as primer for the marker 699. Olgionucleotides of SEQ ID NO:4 and SEQ ID NO:5 were used as primer for the marker 1004. Olgionucleotides of SEQ ID NO:1 and SEQ ID NO:2 were used as primer for the marker standard 1 of the control nucleic acid.

Result: It is known that with increasing deterioration of the quality of the template nucleic acid, the representation of the template nucleic acid after completed WGA becomes increasingly weaker. This was also observed in this experiment: With increasing degradation (fragmentation) of the template nucleic acid, showing due to increasing incubation time (min) of the template nucleic acid with HaeIII, the Ct value increases in the real time analysis of 10 ng WGA DNA (see FIG. 5).

Figure 5:
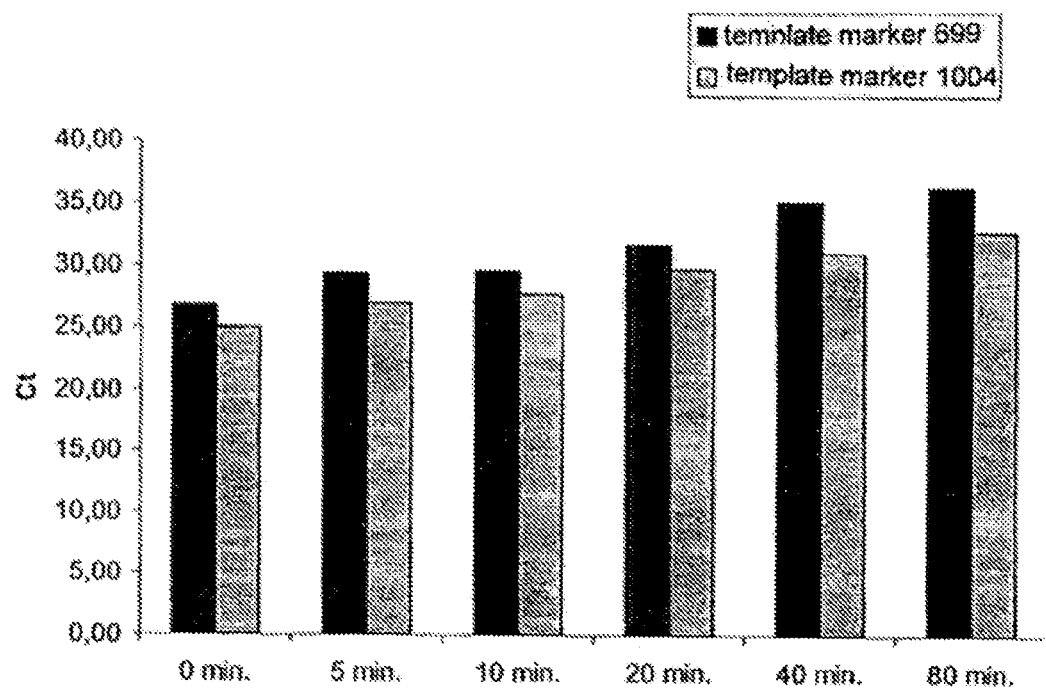
FIG. 5: Representation of the template nucleic acid marker 699 and 1004 in 10 ng WGA DNA. On the Y axis the Ct value from the real time PCR analysis is illustrated. On the X axis the progressive degradation of the template nucleic acid by increase of the incubation period of the template nucleic acid with HaeIII is illustrated.
Figure 6:
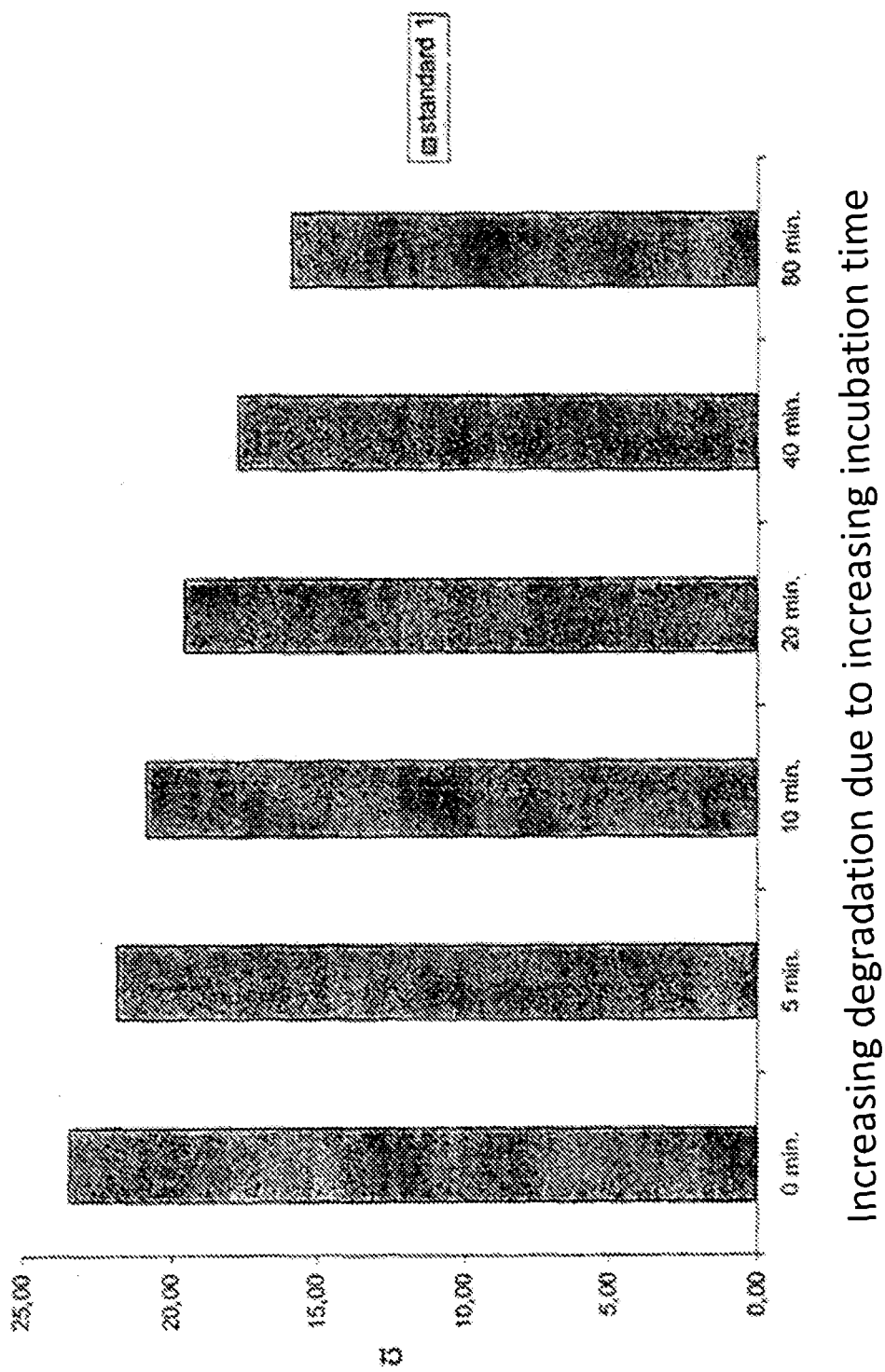
FIG. 6: Representation of the control nucleic acid marker standard 1 in 10 ng WGA DNA. On the Y axis the Ct value from the real time PCR analysis is illustrated. On the X axis the progressive degradation of the template nucleic acid by increase of the incubation period of the template nucleic acid with HaeIII is illustrated.

With regard to the representation of the control nucleic acid after completed WGA, there is a clear correlation with the increase of fragmentation of the originally used complex template nucleic acid (see FIG. 5). The increase of the representation of the control nucleic acid—shown by a decrease of the Ct value of the marker standard 1—correlates with the fragmentation (increase of the HaeIII incubation period) and the decrease of the representation of the template nucleic acid markers (699 and 1004) (cf. FIGS. 4 and 6).

Example 3

Method for the determination of the presence of the template nucleic acid using a control nucleic acid in WGA reactions.

Background: The representation of the control nucleic acid in the total DNA after completed WGA of complex template nucleic acid and control nucleic acid can be indicative for the general presence of the originally used template nucleic acid.

Experiment: A cell culture is diluted in such a way that approximately only every second reaction vessel contains a cell. 20 pg control nucleic acid (Lambda DNA) are added to each reaction vessel. Prior to the WGA, lysis of the cells is carried out. The lysis is carried out according to the REPLI-g® manual. Subsequently, a whole genome amplification is carried out with REPLI-g® reagents (QIAGEN) according to the REPLI-g® manual. After the WGA reaction, the concentration and yield of the DNA is determined by means of the PicoGreen® reagent (see REPLI-g® manual).

The representation of the control DNA and the complex template nucleic acid was analysed in qRT PCR. For this purpose, 10 ng of the total DNA formed in the WGA are used in a qRT-PCR (QuantiTect® real time PCR SYBR® Green Reagents, Qiagen). For the analysis of the representation of the complex template nucleic acid after WGA, the two hexokinase allels HexA and HexG were analysed in the DNA, which was amplified in the WGA, in qRT PCT reactions. For the analysis of the representation of the control nucleic acid after the WGA, the marker standard 1 was used. In this case, too, 10 ng of the amplified total DNA was used each time. The QuantiTect® real time PCR SYBR® Green reagents (Qiagen) were used as qRT PCT reagents.

Figure 7:
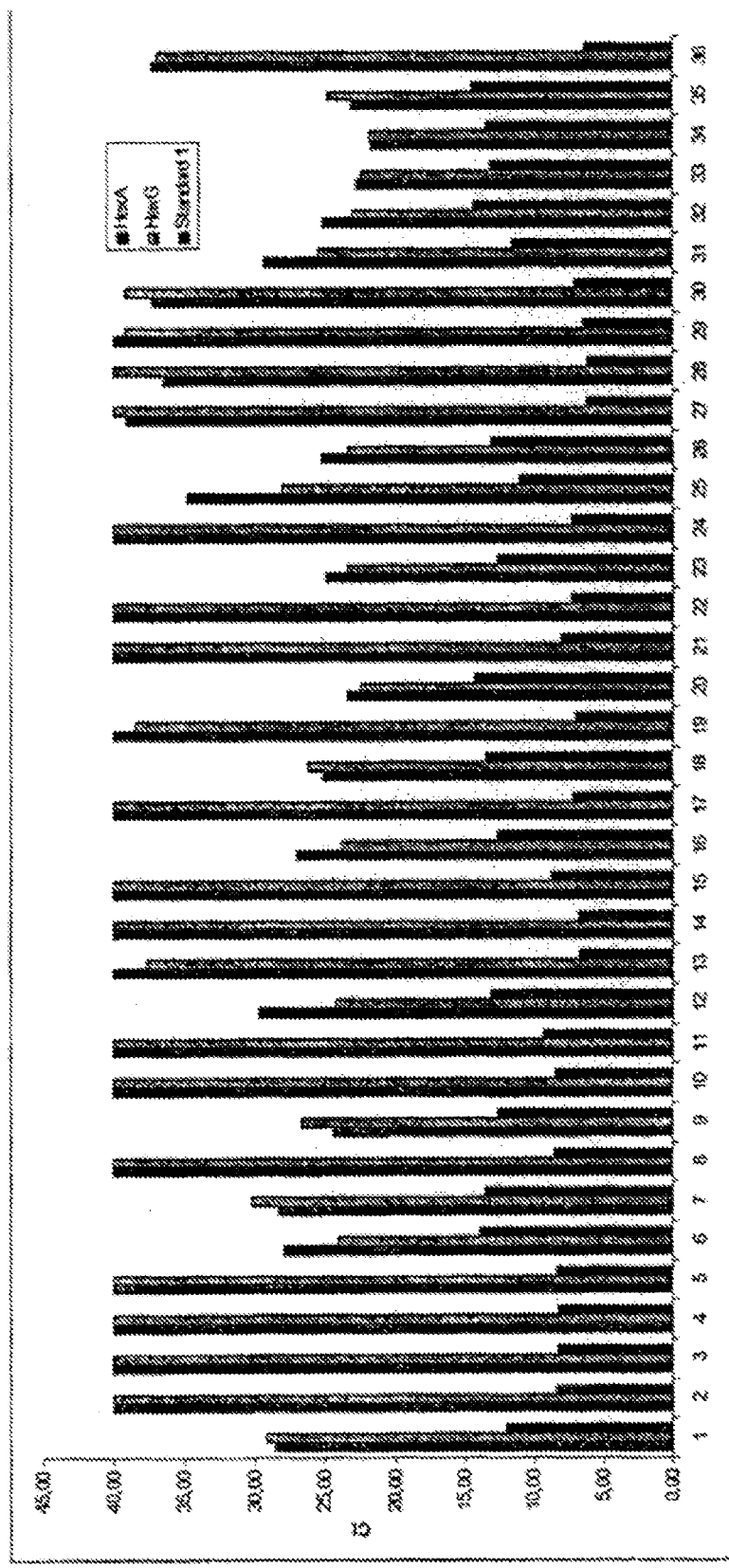
FIG. 7: 36 WGA reactions were carried out, not knowing if the reaction vessel contained a cell (i.e. template nucleic acid) or not. Representation of the control nucleic acid marker standard 1 is always high in the real time PCR (low Ct value of <10) if no template nucleic acid was in the reaction vessel (Ct value ~40 with marker HexA and HexG). If, however, Hex A and Hex G were detected (Ct value ~22 to 30), then the Ct value of the marker was standard 1>10. Thus, the presence of the template nucleic acid can be detected via the control nucleic acid and the subsequent PCR.

Result: Whenever a cell and thus also the complex template nucleic acid was present in the reaction vessel, a Ct value was obtained for the allels HexA and HexG, which was clearly smaller than 40. Such presence clearly correlated with a Ct value of >10 for the marker standard 1, which represents amplification of the control nucleic acid. On average, a value of 13.05 (+/−0.95) was reached. In cases where there was not cell (i.e. no template nucleic acid) present, an average Ct value of 7.5 (+/−0.95) was reached for the marker standard 1. Thus, a Ct value of >10 (marker standard 1) is indicative for the presence of template nucleic acid, whereas a Ct value of <10 indicates the absence of the template nucleic acid (FIG. 7).

The invention claimed is:

1. A method of analyzing one or more complex template nucleic acids, comprising:
   a) providing a reaction mixture comprising:
      (i) at least one complex template nucleic acid to be amplified,
      (ii) at least one control nucleic acid, wherein the control nucleic acid has less than 50% sequence identity to the complex template nucleic acid and wherein said control nucleic acid has at least one known sequence segment,
      (iii) primers for amplifying the complex template nucleic acid, and
      (iv) primers for amplifying the control nucleic acid;
   b) co-amplifying the complex template nucleic acid and the control nucleic acid with a polymerase, wherein the co-amplification takes place isothermally and comprises a strand displacement reaction wherein template and control nucleic acid are amplified;
   c) amplifying the control nucleic acid with a polymerase under the same conditions as the co-amplification of step b) in the absence of the complex template nucleic acid;
   d) quantifying the amplified control nucleic acid from steps b) and c), wherein the quantification is carried out after completion of the co-amplification of step b) and amplification of step c), and wherein said quantification comprises re-amplifying the amplified control nucleic acids using quantitative real time polymerase chain reaction; and
   e) determining the quantity or quality of the complex template nucleic acid present before the co-amplification of step b) based on the quantification of the re-amplified control nucleic acids of step d), wherein quantification of the re-amplified control nucleic acids comprises determining the difference of a Ct value determined for the re-amplified control nucleic acid from the co-amplification of step b) and a Ct value determined for the re-amplified control nucleic acid of step c).

2. The method of claim 1, wherein the control nucleic acid is linear.

3. The method of claim 2, wherein the linear control nucleic acid comprises more than 800 nucleotides.

4. The method of claim 1, wherein the control nucleic acid is circular.

5. The method of claim 1, wherein each of the one or more complex template nucleic acids comprises more than 10,000 nucleotides.

6. The method of claim 1, wherein the one or more complex template nucleic acids are DNA or RNA.

7. The method of claim 1, wherein the one or more complex template nucleic acids comprise one or more genomes, one or more transcriptomes, or one or more bisulfitomes.

8. The method of claim 1, wherein the polymerase used for co-amplification has strand displacement activity.

9. The method of claim 8, wherein the polymerase is a Phi 29-like polymerase, wherein the polymerase occurs in a phage selected from the group consisting of Phi 29, Cp-1, PRD-1, Phi 15, Phi 21, PZE, PZA, Nf, M2Y, B103, SF5, GA-1, Cp-5, Cp-7, PR4, PR5, PR722 and L17.

10. The method of claim 1, wherein the primers used for amplification of the at least one complex template nucleic acid in step b) are also used for the amplification of the one or more control nucleic acids in step b).

11. The method of claim 10, wherein the primers are random primers.

12. The method of claim 1, wherein the quantification of the amplified control nucleic acid is carried out by means of amplification via sequence-specific primers using the at least one known sequence segment.

13. The method of claim 1, wherein the complex template nucleic acid is from a single sample source.

14. The method of claim 13, wherein the single sample source comprises template DNA from multiple organisms.

15. The method of claim 1, wherein the difference of the Ct value determined for the re-amplified control nucleic acid from the co-amplification of step b) and the Ct value determined for the re-amplified control nucleic acid of step c) provides a ΔCt value, wherein the higher the ΔCt value, the higher the quality of the complex template nucleic acid used in the amplification.

16. The method of claim 1, wherein determining the quantity or quality of the complex template nucleic acid present before the co-amplification of step b) is performed in the absence of reamplifying the complex template nucleic acid.

17. A method for standardizing whole-genome, whole-transcriptome, or whole-bisulfitome amplification comprising
   a) providing a reaction mixture comprising:
      (i) at least one complex template nucleic acid to be amplified, wherein the at least one complex template nucleic acid is a nucleic acid from a whole-genome, whole-transcriptome, or whole bisulfitome,
      (ii) at least one control nucleic acid, wherein the control nucleic acid has less than 50% sequence identity to the complex template nucleic acid and wherein said control nucleic acid has at least one known sequence segment,
      (iii) primers for amplifying the complex template nucleic acid, and
      (iv) primers for amplifying the control nucleic acid;
   b) co-amplifying the complex template nucleic acid and the control nucleic acid with a polymerase, wherein the co-amplification takes place isothermally and comprises a strand displacement reaction wherein template and control nucleic acid are amplified;
   c) amplifying the control nucleic acid with a polymerase under the same conditions as the co-amplification of step b) in the absence of the complex template nucleic acid;
   d) quantifying the amplified control nucleic acid from steps b) and c), wherein the quantification is carried out after completion of the co-amplification of step b) and amplification of step c), and wherein said quantification comprises re-amplifying the amplified control nucleic acids using quantitative real time polymerase chain reaction; and
   e) determining the quantity or quality of the complex template nucleic acid present before the co-amplification of step b) based on the quantification of the re-amplified control nucleic acids of step d), wherein quantification of the re-amplified control nucleic acids comprises determining the difference of a Ct value determined for the re-amplified control nucleic acid from the co-amplification of step b) and a Ct value determined for the re-amplified control nucleic acid of step c), wherein the quantity, quality or presence of the complex template nucleic acid provides an internal standard, wherein the internal standard is used to compare reactions that were conducted at different times or different places.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence

```
<220> FEATURE:
<223> OTHER INFORMATION: Description of Artificial Sequence: note =
      synthetic construct

<400> SEQUENCE: 1
gagacgctgg agtacaaacg                                                    20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 2
ccagcggatt atcgccatac tg                                                 22

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 3
tgctccctgt cccatctg                                                      18

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 4
agacagtatg cctttatttc accc                                               24

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 5
gtctttagct gctgaggaaa tg                                                 22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 6
agcagaattc tgcacatgac g                                                  21

<210> SEQ ID NO 7
<211> LENGTH: 21
<212> TYPE: DNA
<213> ORGANISM: Artificial Sequence
<220> FEATURE:
```

```
<223> OTHER INFORMATION: Description of Artificial Sequence: note =
      synthetic construct

<400> SEQUENCE: 7
agtgctaatc tcatgtctct t                                              21

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 8
gctgagagga gtggaagct                                                 19

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 9
agtgctaatg tcatgtctct t                                              21

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 10
gctgagagga gtggaagcc                                                 19
```